United States Patent [19]

Lord et al.

[11] 4,102,582

[45] Jul. 25, 1978

[54] EXAMINATION OF INTERIOR SURFACES USING GLOW-DISCHARGE ILLUMINATION

[75] Inventors: David E. Lord; Richard R. Petrini; Gary W. Carter, all of Livermore, Calif.

[73] Assignee: The United States of America as represented by the United States Department of Energy, Washington, D.C.

[21] Appl. No.: 740,338

[22] Filed: Nov. 9, 1976

[51] Int. Cl.² .......................................... G01N 21/16
[52] U.S. Cl. ............................. 356/241; 250/461 R
[58] Field of Search ................... 356/241; 313/291; 316/1, 22; 250/461 R

[56] References Cited

U.S. PATENT DOCUMENTS

| 2,002,768 | 5/1935 | Erickson | 316/22 |
| 2,541,976 | 2/1951 | Bogart | 356/241 X |
| 2,973,450 | 2/1961 | Restau | 313/291 |

*Primary Examiner*—John K. Corbin
*Assistant Examiner*—Matthew W. Koren
*Attorney, Agent, or Firm*—Dean E. Carlson; Roger S. Gaither; Clifton E. Clouse, Jr.

[57] ABSTRACT

Endoscopic examination of the interior of a hollow structure through a light pipe that is inserted into the structure, the interior being illuminated by means of a glow discharge that is established with a high voltage applied between the structure wall as one electrode and a second electrode that is inserted into the structure, or establishing the glow with two electrodes inserted into the structure.

22 Claims, 3 Drawing Figures

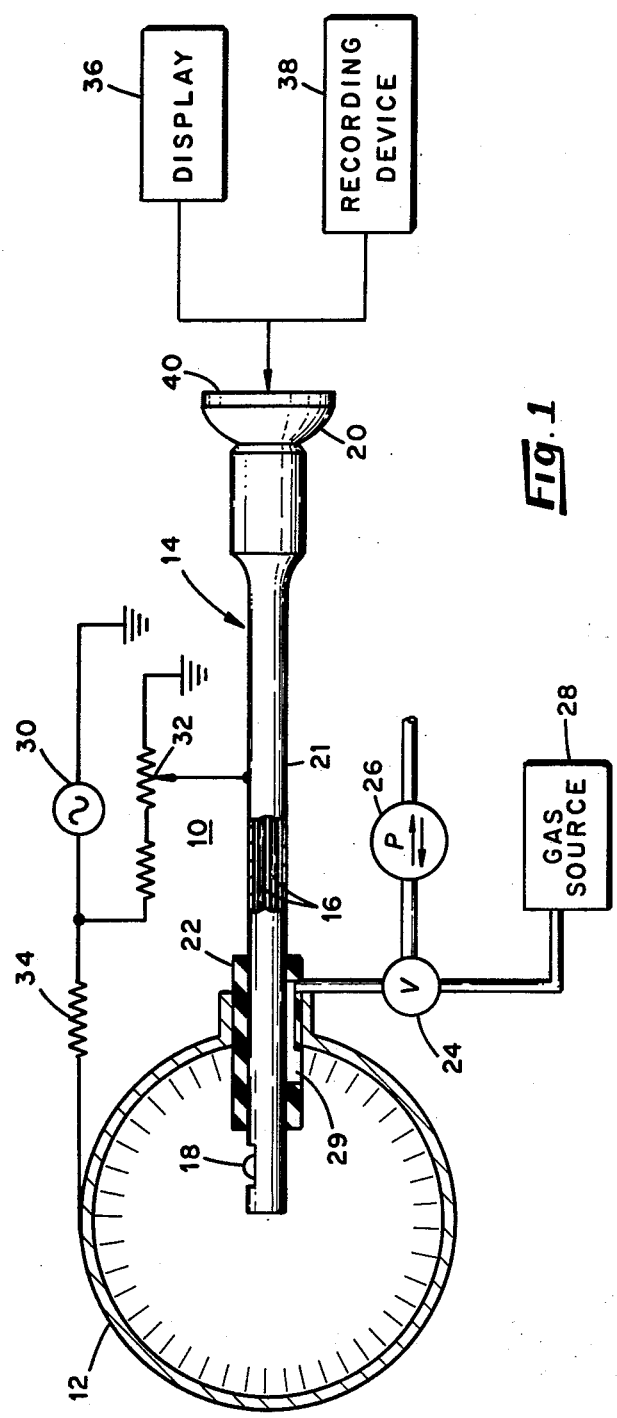

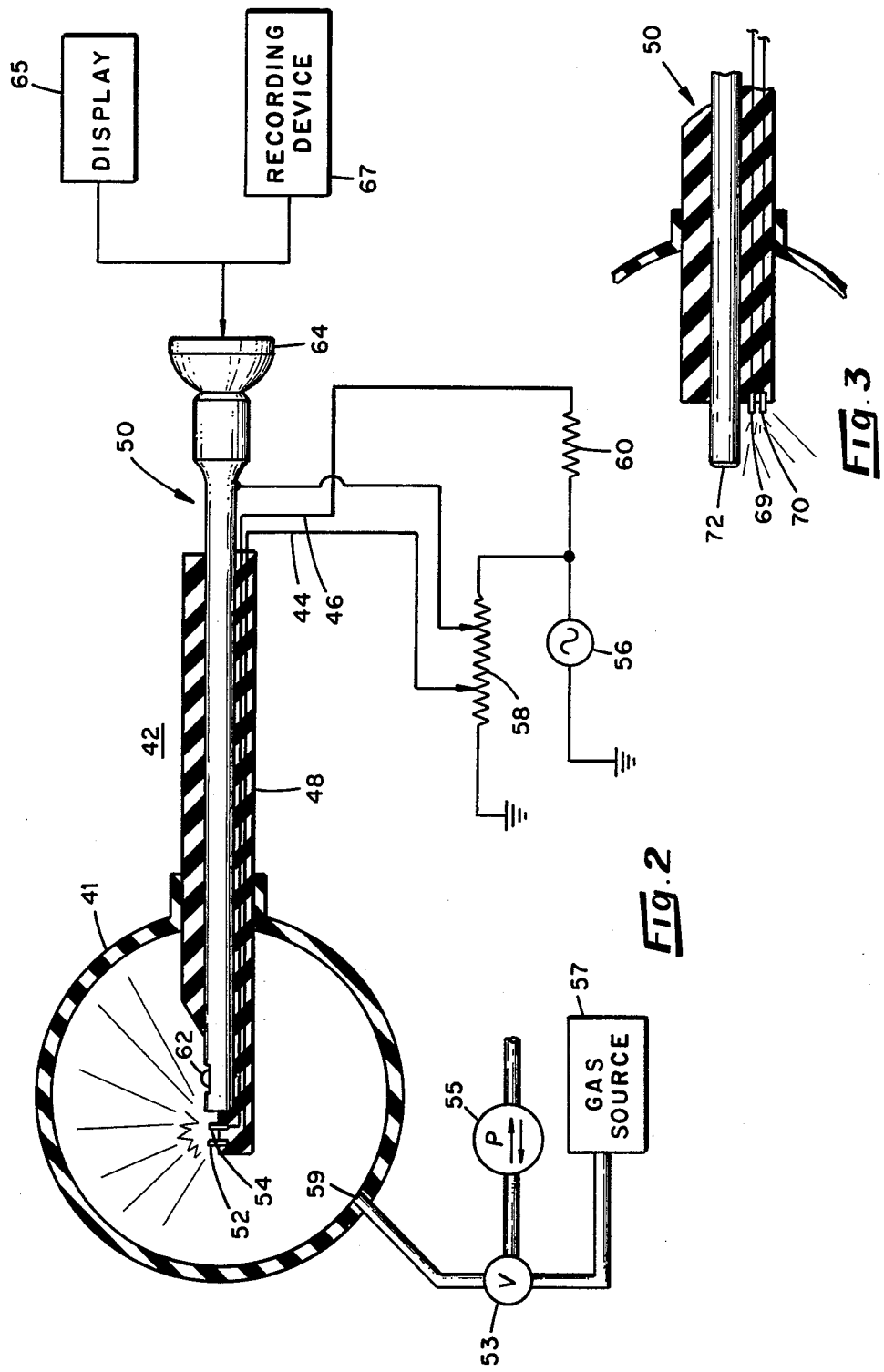

EXAMINATION OF INTERIOR SURFACES USING GLOW-DISCHARGE ILLUMINATION

BACKGROUND OF THE INVENTION

The invention disclosed herein was made under, or in, the course of Contract No. W-7405-ENG-48 with the U.S. Energy Research and Development Administration.

The present invention relates to examination of the interior of hollow structures, and more particularly it relates to such an examination whereby the interior is illuminated by means of a glow discharge.

Examination and inspection of the remote interior of hollow structures, such as heliocopter blades, pipes and tubing in general and heat exchanger tubing for nuclear reactors in particular, may be accomplished by means of endoscopes comprised of thin light pipes including fiber optics for conducting light into the interior to be examined and additional light pipes or rod optics and lenses for conducting light images of the illuminated interior back to an external point for viewing or recording. Alternatively, an electric light source may be inserted with a probe with electrical wires carried by the probe into the interior. Problems encountered with such schemes include low level, incomplete and nonuniform illumination of the interior, and difficulty in illumination with infrared and ultraviolet light. Long thin electric wires and high power electric bulbs are incompatible with the miniaturization generally desired for the small and remote areas often to be examined. In addition for long fiber optics there is a high degradation of light corresponding to the length of fiber used to conduct the illuminating light. Thus for very long distances, the illumination is so low as to render such fiber optic schemes useless. Moreover, endoscopes that require both fibre and rod optics have diameters that are inconveniently large for many uses.

SUMMARY OF THE INVENTION

In brief, the invention is a method for examining the interior surfaces of a hollow structure, comprising the steps of establishing a gaseous ionizable atmosphere within the structure, establishing a glow discharge within the gaseous atmosphere, and examining the interior surfaces of the structure that have been illuminated by the glow discharge.

It is an object of the invention to uniformly and completely illuminate the interior surfaces of a hollow structure for examination.

Another object is to establish a glow discharge in a hollow structure for examination of the interior surfaces of the structure.

Another object is to maximize the length over which an endoscopic examination may effectively be performed within a hollow structure.

Another object is to simply and effectively illuminate the interior of a hollow structure with a light of a selected wavelength.

Another object is to reduce the diameter of endoscopes by the elimination of fibre optics.

Other objects and advantageous features of the invention will be apparent in a description of a specific embodiment thereof, given by way of example only, to enable one skilled in the art to readily practice the invention which is described hereinafter with reference to the accompanying drawing.

BRIEF DESCRIPTION OF THE DRAWING

FIG. 1 is a diagram partially in cross section of a hollow electrically conductive structure fitted with an endoscope, and including a schematic diagram of a voltage source applied across the structure and the endoscope for establishing a glow discharge within the structure to illuminate the interior surfaces of the structure for viewing with the endoscope, according to the invention.

FIG. 2 is a diagram partially in cross section of a hollow structure of electrically nonconducting material, that is fitted with an endoscope, and including a schematic diagram of a voltage source applied across two electrodes inserted into the vessel with the endoscope for establishing a glow discharge within the structure to illuminate the interior surfaces of the structure for viewing with the endoscope.

FIG. 3 is a diagram partially in cross section of a variation of the electrode and endoscope arrangement of FIG. 2.

DESCRIPTION OF AN EMBODIMENT

Referring to the drawing there is shown in FIG. 1 an arrangement 10 for examining the interior of a hollow electrically conductive structure 12. The arrangement 10 includes an endoscope 14 that may be inserted into the interior of the structure 12. The endoscope is comprised of a bundle of thin light pipes 16 of the rod optic type that optically connect a lens 18 on the insertable end of the endoscope to an external eyepiece 20. The light pipes 16 are enclosed in an electrically conductive case 21 which is electrically insulated from the structure 12 by means of an insulating sleeve 22. If a conventional endoscope is used it will also have fibre optics in addition to rod optics, but the fibre optics simply are not used in practicing the invention.

In performance of the method of the invention the structure 12 is filled with air or other gas, usually below atmospheric pressure, by means of a valve 24, a two-way pump 26, and/or gas source 28, all of which may conveniently be connected to the interior of the structure through a passage 29 in the sleeve 22. A voltage from a source 30 is applied across the structure 12 and the case 21. The voltage is adjusted by means of a potentiometer 32 to a level that causes ionization and a glow discharge of the gas in the structure. A current-limiting resistor 34 is provided to minimize the occurrence of arcing; and the source 30 is preferably an AC source to further minimize the occurrence of arcing, and thereby maintain an even glow discharge. The glow discharge thus created uniformly and completely illuminates the interior of the structure. This enables the lens 18 to transmit full and complete images of the interior of the structure 12 through the rod optics to the eyepiece 20 for direct viewing, or for viewing on a display 36 such as a television screen, or for recording by means of a device 38 such as on photographic film. The endoscope may be further inserted or withdrawn and also rotated for full viewing of the structure interior. The eyepiece 20 also may be provided with an appropriate filter 40 to enable viewing of the structure interior at a selected wavelength. Since a glow discharge produces the full spectrum of light waves, the wavelength selected may range from ultraviolet through visible to infrared. For example, viewing only certain fluorescent wavelengths permits ultraviolet responsive fluorescent penetrants to be used to lodge in and make internal flaws of the structure 12 visible under ultraviolet radiation. This use in conjunction with thick-walled pressure vessels provides a means of early detection of cracks which normally initiate at the higher stressed inside surface region. Also the emission peak of the glow discharge may be selected by the choice of gas present in the structure to provide the most suitable peak for the wavelengths to be viewed.

In practice of the invention, the structure 12 was evacuated to from 3–5 torr of air; applied potentials from the source 30 were in the range of 2–10 kilovolts AC at 100–10,000 Hz; and the glow-discharge emission peaks included those of atmospheric nitrogen, argon, and neon, which peaks were obtained by varying the amount of these gases within the structure. Also, each of these gases was found to provide a glow discharge rich in ultraviolet radiation.

For operation of the arrangement 10 at atmospheric pressure or higher, higher applied voltages are necessary. However, the foregoing specified pressure and voltage ranges are easily handled with readily available equipment.

If the structure to be examined is made of electrically nonconducting material such as a structure 41 (FIG. 2) or it is desirable not to apply a voltage to the structure an alternative arrangement 42 may be used. In this arrangement, two high voltage wires 44 and 46 are embedded in a sleeve 48 of electrical insulation around an endoscope 50. The wires terminate as exposed electrodes 52 and 54 inside the structure 41 which is filled with an ionizable gas by means of a valve 53, pump 55 and gas source 57, all connected to the interior of the structure such as through a passage 59. A voltage from a source 56 is applied through a voltage divider 58, current limiting resistor 60 and the wires 44 and 46 to the electrodes 52 and 54 to produce a glow discharge in the gas within the structure 41. The electrodes 52 and 54 are oriented transversely to the length of the endoscope to establish the glow discharge to illuminate the interior of the structure that faces a lens 62, also transversely oriented, at the interior end of the endoscope 50. The images of the interior of the structure may be viewed externally either directly or through a filter 64. The endoscope 50 may be fully inserted, withdrawn and rotated to obtain multiple images of the interior of the structure. A display device 65 or recording device 67 may also be used for such as television viewing or photographic recording.

The lens-electrode arrangement at the end of the endoscope 50 may also be of alternative configurations such as the one shown in FIG. 3 wherein electrodes 69 and 70 are oriented parallel to the length of the endoscope and a lens 72 is mounted to receive light generally parallel to the endoscope length. While an embodiment of the invention has been shown and described, further embodiments or combinations of those described herein will be apparent to those skilled in the art without departing from the spirit of the invention. For example, both of the electrodes to establish the glow discharge may be separate from the endoscope.

What we claim is:

1. A method for examining the interior surfaces of a hollow structure including the steps of:
    filling the interior of the hollow structure with an ionizable gas;
    ionizing the gas to produce a glow discharge in the gas to illuminate the interior surfaces of the structure; and
    examining the glow discharge illuminated surfaces of the structure with a viewing means including a portion positioned within the structure.

2. The method of claim 1, wherein said step of ionizing the gas includes applying a voltage across two electrodes in contact with the gas within the hollow structure to ionize the gas and establish a glow discharge.

3. The method of claim 2, wherein the structure is made of electrically conductive material and said step of ionizing the gas includes inserting an electrode into the hollow structure, and applying the voltage across the hollow structure as one electrode and the inserted electrode as the other.

4. The method of claim 2, wherein said step of ionizing the gas includes inserting two electrodes into the hollow structure and applying the ionizing voltage across the two electrodes.

5. The method of claim 2, wherein the voltage applied across the electrodes is an alternating current voltage.

6. The method of claim 5, wherein the applied voltage is in the range of 2–10 KV at 100 to 10,000 Hz and the gas is within a pressure range of 2–5 torr.

7. The method of claim 1, wherein the step of filling the structure includes adjusting the pressure of the gas within the hollow structure to be less than atmospheric.

8. The method of claim 1, wherein the step of filling includes filling the structure with a gas selected to have a peak intensity at a predetermined wavelength.

9. The method of claim 1, wherein the step of examining the illuminated interior surfaces includes inserting an endoscope into the interior of the structure.

10. The method of claim 9, wherein the optical system of the endoscope is comprised solely of rod optics for transmitting light from the structure interior to the viewing end of the endoscope.

11. The method of claim 9, wherein the examining step includes placing a filter over the outer end of the endoscope for transmission of a selected wavelength of light from the endoscope.

12. The method of claim 9, further including the step of photographically recording the images of the interior surfaces transmitted through the endoscope.

13. The method of claim 9, wherein said step of examining includes forming television signals of the images transmitted through the endoscope for transmission to a television screen for viewing the interior surfaces of the structure.

14. The method of claim 1, further including the steps of applying an ultraviolet responsive penetrant to the interior surfaces of the hollow structure and viewing the surface images through a filter selected to pass only the fluorescent wavelengths of said penetrant.

15. The method of claim 14, wherein said step of filling includes filling the structure with a gas that emits a peak intensity at the ultraviolet wavelength to which the penetrant is responsive under a glow-discharge condition of the gas.

16. An arrangement for examining the interior surfaces of a hollow structure, including:
    means for filling the interior of the structure with an ionizable gas;
    means for ionizing the gas to produce a glow-discharge in the gas to illuminate the interior surfaces of the structure; and
    means for examining the glow-discharge illuminated surfaces of the structure, said examining means including a portion positioned within the interior of the structure.

17. The arrangement of claim 16, wherein said ionizing means includes first and second electrodes in contact with the gas, and a voltage applied across said electrodes.

18. The arrangement of claim 17, wherein the structure is made of electrically conductive material and is used as said first electrode and said second electrode is inserted into the hollow structure.

19. The arrangement of claim 17, wherein said first and second electrodes are inserted into the hollow structure.

20. The arrangement of claim 17, wherein said examining means includes an endoscope including an outer case of electrically conductive material, and said voltage source is applied across said structure as said first electrode and said endoscope case as said second electrode.

21. The arrangement of claim 17, wherein said examining means includes an endoscope, and said first and second electrodes are carried by said endoscope into contact with the gas.

22. The arrangement of claim 17, wherein said examining means is an endoscope having an optical system comprised solely of rod optics.

* * * * *